(12) United States Patent
Cooper et al.

(10) Patent No.: US 8,309,136 B2
(45) Date of Patent: *Nov. 13, 2012

(54) IN VITRO METHODS FOR EVALUATING THE IN VIVO EFFECTIVENESS OF DOSAGE FORMS OF MICROPARTICULATE OR NANOPARTICULATE ACTIVE AGENT COMPOSITIONS

(75) Inventors: Eugene R. Cooper, Berwyn, PA (US); John A. Bullock, King of Prussia, PA (US); John R. Chippari, Phonenixville, PA (US); John L. Schaefer, Gilbertsville, PA (US); Rakesh A. Patel, Bensalem, PA (US); Rajeev Jain, Farmingham, MA (US); Joost Strasters, Exton, PA (US); Niels P. Ryde, Malvern, PA (US); Stephen B. Ruddy, Schwenksville, PA (US)

(73) Assignee: Alkermes Pharma Ireland Limited, Dublin (IE)

( * ) Notice: Subject to any disclaimer, the term of this patent is extended or adjusted under 35 U.S.C. 154(b) by 82 days.

This patent is subject to a terminal disclaimer.

(21) Appl. No.: 12/729,018

(22) Filed: Mar. 22, 2010

(65) Prior Publication Data

US 2010/0178648 A1 Jul. 15, 2010

Related U.S. Application Data

(63) Continuation of application No. 11/650,412, filed on Jan. 8, 2007, now Pat. No. 7,695,739, which is a continuation of application No. 10/323,736, filed on Dec. 20, 2002, now Pat. No. 7,198,795, which is a continuation-in-part of application No. 10/075,443, filed on Feb. 15, 2002, now Pat. No. 6,592,903, which is a continuation of application No. 09/666,539, filed on Sep. 21, 2000, now Pat. No. 6,375,986.

(51) Int. Cl.
*A61K 9/16* (2006.01)
*A61K 9/14* (2006.01)

(52) U.S. Cl. ............ 424/489; 424/434; 424/45; 424/46; 424/466; 424/501

(58) Field of Classification Search ............... 424/489, 424/434, 45, 46, 466, 501
See application file for complete search history.

(56) References Cited

U.S. PATENT DOCUMENTS

| | | |
|---|---|---|
| 3,269,798 A | 8/1966 | Preston |
| 3,692,532 A | 9/1972 | Shankenberq et al. |
| 4,225,581 A | 9/1980 | Kreuter et al. |
| 4,389,397 A | 6/1983 | Lo et al. |
| 4,524,060 A | 6/1985 | Mughal et al. |
| 4,540,602 A | 9/1985 | Motoyama et al. |
| 4,562,069 A | 12/1985 | Hegasy et al. |
| 4,657,901 A | 4/1987 | Ueda et al. |
| 4,665,081 A | 5/1987 | Doi et al. |
| 4,727,077 A | 2/1988 | Haga et al. |
| 4,757,059 A | 7/1988 | Sorenson |
| 4,765,990 A | 8/1988 | Sugimoto et al. |
| 4,783,484 A | 11/1988 | Violante et al. |
| 4,814,175 A | 3/1989 | Tack et al. |
| 4,826,689 A | 5/1989 | Violanto et al. |
| 4,851,421 A | 7/1989 | Iwasaki et al. |
| 4,863,742 A | 9/1989 | Panoz et al. |
| 4,880,634 A | 11/1989 | Speiser |
| 4,895,726 A | 1/1990 | Curtet et al. |
| 4,904,668 A | 2/1990 | Kondo et al. |
| 4,917,816 A | 4/1990 | Self |
| 4,983,605 A | 1/1991 | Kondo et al. |
| 4,997,454 A | 3/1991 | Violante et al. |
| 5,002,952 A | 3/1991 | Kondo et al. |
| 5,024,843 A | 6/1991 | Kuczynski et al. |
| 5,049,322 A | 9/1991 | Devissaguet et al. |
| 5,098,907 A | 3/1992 | Kondo et al. |
| 5,110,605 A | 5/1992 | Acharya |
| 5,118,528 A | 6/1992 | Fessi et al. |
| 5,133,908 A | 7/1992 | Stainmesse et al. |
| 5,145,684 A | 9/1992 | Liversidge et al. |
| 5,156,767 A | 10/1992 | Fitzgerald et al. |
| 5,188,755 A | 2/1993 | Chang |
| 5,215,758 A | 6/1993 | Krishnamurthy |
| 5,260,478 A | 11/1993 | Bacon et al. |
| 5,264,213 A | 11/1993 | Shibahara et al. |
| 5,264,610 A | 11/1993 | Bacon |
| 5,298,262 A | 3/1994 | Na et al. |
| 5,300,739 A | 4/1994 | Bittar |
| 5,302,401 A | 4/1994 | Liversidge et al. |
| 5,318,767 A | 6/1994 | Liversidge et al. |
| 5,326,552 A | 7/1994 | Na et al. |
| 5,328,404 A | 7/1994 | Bacon et al. |
| 5,336,507 A | 8/1994 | Na et al. |
| 5,338,761 A | 8/1994 | Nakajima et al. |

(Continued)

FOREIGN PATENT DOCUMENTS

CA 2346001 4/2000

(Continued)

OTHER PUBLICATIONS

Office Action cited in related U.S. Appl. No. 12/292,395, dated May 26, 2010.
Office Action cited in related U.S. Appl. No. 11/979,240, dated Dec. 16, 2009.
Notice of Reasons for Rejection cited in related Japanese Patent Application No. 2004-510760 dated Dec. 2, 2009, 4 pgs.
Notice of Reasons for Rejection cited in related Japanese Patent Application No. 2004-521891 dated Dec. 22, 2009, 3 pgs.
Office Action cited in related U.S. Appl. No. 11/979,231, dated Mar. 16, 2010.
Office Action cited in related U.S. Appl. No. 11/980,720, dated Mar. 29, 2010.
Butler et al., "Effects of Protein Stabilizing Agents on Thermal Backbone Motions: A Disulfide Trapping Study," *Biochemistry*, vol. 35, pp. 10595-10600 (1996).
Office Action cited in related U.S. Appl. No. 09/337,675, dated Feb. 18, 2010.

(Continued)

*Primary Examiner* — Mina Haghighatian
(74) *Attorney, Agent, or Firm* — Foley & Lardner LLP

(57) ABSTRACT

Disclosed are in vitro methods for evaluating the in vivo redispersibility of dosage forms of poorly water-soluble active agents. The methods utilize media representative of in vivo human physiological conditions.

14 Claims, 2 Drawing Sheets

U.S. PATENT DOCUMENTS

| | | | |
|---|---|---|---|
| 5,340,564 A | 8/1994 | Illig et al. |
| 5,346,702 A | 9/1994 | Na et al. |
| 5,349,957 A | 9/1994 | Yudelson |
| 5,352,459 A | 10/1994 | Hollister et al. |
| 5,356,467 A | 10/1994 | Oshlack et al. |
| 5,384,124 A | 1/1995 | Courteille et al. |
| 5,399,353 A | 3/1995 | Bartnik et al. |
| 5,399,363 A | 3/1995 | Liversidge et al. |
| 5,401,492 A | 3/1995 | Kellar et al. |
| 5,429,824 A | 7/1995 | June |
| 5,447,710 A | 9/1995 | Na et al. |
| 5,451,393 A | 9/1995 | Liversidge et al. |
| 5,466,433 A | 11/1995 | Bacon et al. |
| 5,466,440 A | 11/1995 | Ruddy et al. |
| 5,470,583 A | 11/1995 | Na et al. |
| 5,472,683 A | 12/1995 | Illig |
| 5,494,683 A | 2/1996 | Liversidge et al. |
| 5,500,204 A | 3/1996 | Osifo |
| 5,503,723 A | 4/1996 | Ruddy et al. |
| 5,510,118 A | 4/1996 | Swanson et al. |
| 5,518,187 A | 5/1996 | Bruno et al. |
| 5,518,738 A | 5/1996 | Eickhoff et al. |
| 5,521,168 A | 5/1996 | Clark |
| 5,521,218 A | 5/1996 | Osifo |
| 5,525,328 A | 6/1996 | Bacon et al. |
| 5,534,270 A | 7/1996 | De Castro |
| 5,542,935 A | 8/1996 | Unger et al. |
| 5,543,133 A | 8/1996 | Swanson et al. |
| 5,552,160 A | 9/1996 | Liversidge et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,749 A | 11/1996 | Illig |
| 5,573,750 A | 11/1996 | Singh |
| 5,573,783 A | 11/1996 | Desieno et al. |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,593,657 A | 1/1997 | Ruddy et al. |
| 5,595,762 A | 1/1997 | Derrieu et al. |
| 5,603,916 A | 2/1997 | Singh |
| 5,622,938 A | 4/1997 | Wong |
| 5,628,981 A | 5/1997 | Liversidge et al. |
| 5,632,996 A | 5/1997 | Ramirez et al. |
| 5,643,552 A | 7/1997 | Illig |
| 5,656,299 A | 8/1997 | Kino et al. |
| 5,665,330 A | 9/1997 | Wong |
| 5,665,331 A | 9/1997 | Bagchi et al. |
| 5,668,196 A | 9/1997 | Robinson et al. |
| 5,670,136 A | 9/1997 | Bacon et al. |
| 5,716,642 A | 2/1998 | Bagchi et al. |
| 5,718,388 A | 2/1998 | Czekai et al. |
| 5,718,919 A | 2/1998 | Ruddy et al. |
| 5,719,197 A | 2/1998 | Kanios et al. |
| 5,741,522 A | 4/1998 | Violante et al. |
| 5,747,001 A | 5/1998 | Wiedmann et al. |
| 5,756,546 A | 5/1998 | Pirotte et al. |
| 5,776,496 A | 7/1998 | Violante et al. |
| 5,795,909 A | 8/1998 | Shashoua et al. |
| 5,811,388 A | 9/1998 | Friend et al. |
| 5,811,404 A | 9/1998 | De Frees et al. |
| 5,811,422 A | 9/1998 | Lam et al. |
| 5,811,425 A | 9/1998 | Woods et al. |
| 5,834,025 A | 11/1998 | De Garavilla et al. |
| 5,853,756 A | 12/1998 | Mody et al. |
| 5,862,999 A | 1/1999 | Czekai et al. |
| 5,871,747 A | 2/1999 | Gengoux-Sedilik et al. |
| 5,889,088 A | 3/1999 | Kisuno et al. |
| 5,904,929 A | 5/1999 | Uekama et al. |
| 5,916,596 A | 6/1999 | Desai et al. |
| 5,939,091 A | 8/1999 | Eoga et al. |
| 5,972,389 A | 10/1999 | Shell et al. |
| 6,001,928 A | 12/1999 | Harkness et al. |
| 6,004,582 A | 12/1999 | Faour et al. |
| 6,017,932 A | 1/2000 | Singh et al. |
| 6,045,829 A | 4/2000 | Liversidge et al. |
| 6,068,858 A | 5/2000 | Liversidge et al. |
| 6,090,830 A | 7/2000 | Myers et al. |
| 6,093,420 A | 7/2000 | Baichwal |
| 6,117,455 A | 9/2000 | Takada et al. |
| 6,153,225 A | 11/2000 | Lee et al. |
| 6,165,506 A | 12/2000 | Jain et al. |
| 6,177,103 B1 | 1/2001 | Pace et al. |
| 6,177,104 B1 | 1/2001 | Allen et al. |
| 6,193,960 B1 | 2/2001 | Metzger et al. |
| 6,221,400 B1 | 4/2001 | Liversidge et al. |
| 6,231,888 B1 | 5/2001 | Lerner et al. |
| 6,264,922 B1 | 7/2001 | Wood et al. |
| 6,267,989 B1 | 7/2001 | Liversidge et al. |
| 6,270,806 B1 | 8/2001 | Liversidge et al. |
| 6,303,147 B1 | 10/2001 | Gilis |
| 6,316,029 B1 | 11/2001 | Jain et al. |
| 6,368,620 B2 | 4/2002 | Liu et al. |
| 6,375,986 B1 | 4/2002 | Ryde et al. |
| 6,383,471 B1 | 5/2002 | Chen et al. |
| 6,395,300 B1 | 5/2002 | Straub et al. |
| 6,428,814 B1 | 8/2002 | Bosch |
| 6,432,381 B2 | 8/2002 | Liversidge et al. |
| 6,458,373 B1 | 10/2002 | Lambert et al. |
| 6,458,777 B1 | 10/2002 | Sonis et al. |
| 6,579,352 B1 | 6/2003 | Tanaka et al. |
| 6,592,903 B2 | 7/2003 | Ryde et al. |
| 6,696,084 B2 | 2/2004 | Pace et al. |
| 6,811,767 B1 | 11/2004 | Bosch et al. |
| 6,969,529 B2 | 11/2005 | Bosch et al. |
| 7,198,795 B2 | 4/2007 | Cooper et al. |
| 7,244,451 B2 | 7/2007 | Bosch et al. |
| 7,288,267 B2 | 10/2007 | Bosch et al. |
| 7,459,283 B2 | 12/2008 | Wertz et al. |
| 7,521,068 B2 | 4/2009 | Bosch et al. |
| 7,695,739 B2 | 4/2010 | Cooper et al. |
| 7,850,995 B2 | 12/2010 | Bosch et al. |
| 2002/0002294 A1 | 1/2002 | Cushman et al. |
| 2002/0012675 A1 | 1/2002 | Jain et al. |
| 2002/0055462 A1 | 5/2002 | Reed et al. |
| 2002/0165265 A1 | 11/2002 | Hunter et al. |
| 2003/0077329 A1 | 4/2003 | Kipp et al. |
| 2004/0013613 A1 | 1/2004 | Jain et al. |
| 2004/0013734 A1 | 1/2004 | Babcock et al. |
| 2004/0033267 A1 | 2/2004 | Merisko-Liversidge et al. |
| 2004/0057993 A1 | 3/2004 | Jain et al. |
| 2004/0101566 A1 | 5/2004 | Cooper et al. |
| 2004/0115134 A1 | 6/2004 | Merisko-Liversidge |
| 2004/0141925 A1 | 7/2004 | Bosch et al. |
| 2004/0156872 A1 | 8/2004 | Bosch et al. |
| 2004/0198644 A1 | 10/2004 | Bender et al. |
| 2004/0258757 A1 | 12/2004 | Bosch et al. |
| 2005/0004049 A1 | 1/2005 | Liversidge |
| 2005/0019412 A1 | 1/2005 | Bosch et al. |
| 2007/0048378 A1 | 3/2007 | Swanson et al. |
| 2007/0160675 A1 | 7/2007 | Devane et al. |
| 2008/0003295 A1 | 1/2008 | Bosch et al. |
| 2008/0124393 A1 | 5/2008 | Swanson et al. |
| 2008/0213378 A1 | 9/2008 | Cooper et al. |
| 2008/0248123 A1 | 10/2008 | Swanson et al. |
| 2009/0047209 A1 | 2/2009 | Merisko-Liversidge |
| 2009/0130213 A1 | 5/2009 | Jain et al. |
| 2011/0027371 A1 | 2/2011 | Cooper et al. |

FOREIGN PATENT DOCUMENTS

| | | |
|---|---|---|
| EP | 0 220 760 A2 | 10/1985 |
| EP | 0 220 143 | 4/1987 |
| EP | 0 262 560 A2 | 9/1987 |
| EP | 0 275 796 | 7/1988 |
| EP | 0 375 662 | 6/1990 |
| EP | 0 486 153 A2 | 5/1992 |
| EP | 0 600 532 A2 | 6/1994 |
| EP | 0 601 619 A2 | 6/1994 |
| EP | 0 602 702 A1 | 6/1994 |
| EP | 0 601 619 | 6/1994 |
| EP | 0 577 215 | 3/2000 |
| EP | 1 010 435 A1 | 6/2000 |
| EP | 1 800 666 A1 | 6/2007 |
| FR | 2304326 | 9/1979 |

| | | |
|---|---|---|
| GB | 2 166 651 | 5/1986 |
| GB | 2316316 A | 2/1998 |
| JP | 48-043848 | 11/1970 |
| JP | 57-26615 | 2/1982 |
| JP | 61-218516 | 9/1986 |
| JP | 62-126127 | 6/1987 |
| JP | 63-005021 | 1/1988 |
| JP | 63-240936 | 10/1988 |
| JP | 2-167222 | 6/1990 |
| JP | 03/066613 | 3/1991 |
| JP | 4-502318 | 4/1992 |
| JP | 4-295420 | 10/1992 |
| JP | 6-227967 | 8/1994 |
| JP | 07-112936 | 5/1995 |
| JP | 8-151322 | 6/1996 |
| JP | 8-507075 | 7/1996 |
| JP | 8-259460 | 10/1996 |
| JP | 9-241178 | 9/1997 |
| JP | 09-271658 | 10/1997 |
| JP | 2004-513886 | 5/2004 |
| WO | WO 90/15593 | 12/1990 |
| WO | WO 91/13612 | 9/1991 |
| WO | WO 93-10760 | 6/1993 |
| WO | WO 93/10760 | 6/1993 |
| WO | WO 93/10767 | 6/1993 |
| WO | WO 93/13773 | 7/1993 |
| WO | WO 93/25190 | 12/1993 |
| WO | WO 93/25194 | 12/1993 |
| WO | WO 93/25195 | 12/1993 |
| WO | WO 94/18954 | 9/1994 |
| WO | WO 94/20072 | 9/1994 |
| WO | WO 95/05164 | 2/1995 |
| WO | WO 95/22318 A1 | 8/1995 |
| WO | WO 95/27475 | 10/1995 |
| WO | WO 96/03132 A1 | 2/1996 |
| WO | WO 96/20698 | 7/1996 |
| WO | WO 96/20698 A2 | 7/1996 |
| WO | WO 96/24335 | 8/1996 |
| WO | WO 96/25918 | 8/1996 |
| WO | WO 97/18796 | 5/1997 |
| WO | WO 98/04291 | 2/1998 |
| WO | WO 98/07414 | 2/1998 |
| WO | WO 98/14174 | 4/1998 |
| WO | WO 98/29098 | 7/1998 |
| WO | WO 98/31360 | 7/1998 |
| WO | WO 98/35666 | 8/1998 |
| WO | WO 99/02665 | 1/1999 |
| WO | WO 99/25354 | 5/1999 |
| WO | WO 99/38493 | 8/1999 |
| WO | WO 99/65469 | 12/1999 |
| WO | WO 00/13672 | 3/2000 |
| WO | WO 00/18374 | 4/2000 |
| WO | WO 00/27363 | 5/2000 |
| WO | WO 00/32189 | 6/2000 |
| WO | WO 00/47196 | 8/2000 |
| WO | WO 00/51572 | 9/2000 |
| WO | WO 0053164 | 9/2000 |
| WO | WO 01/17546 A1 | 3/2001 |
| WO | WO 01/26635 | 4/2001 |
| WO | WO 01/45674 | 6/2001 |
| WO | WO 01/78505 A1 | 10/2001 |
| WO | WO 01/78680 A2 | 10/2001 |
| WO | WO 01/91750 A1 | 12/2001 |
| WO | WO 01/92584 A1 | 12/2001 |
| WO | WO 02/24163 | 3/2002 |
| WO | WO 02/067901 A1 | 9/2002 |
| WO | WO 02/098565 | 12/2002 |
| WO | WO 03/080027 A1 | 10/2003 |
| WO | WO 03/094894 A1 | 11/2003 |
| WO | WO 03/103633 A1 | 12/2003 |

OTHER PUBLICATIONS

Canadian Office Action for related Canadian Patent Application No. 2,488,499, dated Feb. 8, 2010.

Notice of Reasons for Rejection cited in related Japanese Patent Application No. 2003-565446, dated Jan. 20, 2010, 4 pgs.

Office Action cited in related U.S. Appl. No. 10/697,703, dated Feb. 18, 2010.

Office Action cited in related U.S. Appl. No. 10/667,470, dated Dec. 29, 2009.

Decision on Rejection cited in related Japanese Patent Application No. 2001-583733, dated Jun. 9, 2010, 3 pgs.

"Design and Evaluation of Oral Administration Drug Formulation", *Pharmaceutical Industry Time Signal Company*, pp. 167-168 (1995).

Kondo et al., "Improved Oral Absorption of Enteric Coprecipitates of a Poorly Soluble Drug," *J. Pharm. Sciences*, 83(4):566-570 (1994).

Kondo et al., "Improved Oral Absorption of a Poorly Water-Soluble Drug, HO-221, by Wet-Bead Milling Producing Particles in Submicron Region," *Chem. Pharm. Bull.*, 41(4):737-740 (1993).

Kondo, et al, "Pharmacokinetics of a Micronized, Poorly Water Soluble Drug, HO-221, in Experimental Animals," *Biol. Pharm. Bull.*, 16(8):796-800 (1993).

Office Action dated Nov. 12, 2008 for related U.S. Appl. No. 10/667,470, 20 pgs.

Office Action dated Sep. 18, 2008 for related U.S. Appl. No. 11/979,231, 11 pgs.

Office Action cited in related U.S. Appl. No. 11/650,412 dated May 12, 2009.

Notice of Rejections completed Aug. 24, 2009 for related Japanese Patent Application No. 2002-590934, and Notice of Rejections completed Apr. 24, 2008 listing documents A1-A10 and prior art references 1-5.

Canadian Office Action dated Jul. 6, 2010 cited in related Canadian Patent Application No. 2,492,488, 3 pgs.

Office Action cited in related U.S. Appl. No. 10/667,470, dated Jul. 27, 2010.

Office Action cited in related U.S. Appl. No. 10/701,064, dated Feb. 14, 2011.

Office Action cited in related U.S. Appl. No. 12/292,395, dated Dec. 6, 2010.

Office Action cited in related U.S. Appl. No. 11/980,720, dated Dec. 22, 2010.

European Search Report cited in related EP Patent Application No. EP 10010944, dated Dec. 13, 2010.

Canadian Office Action cited in related Canadian Patent Application No. 2475092, dated Jan. 11, 2011.

Calvo et al., "Effect of lysozyme on the stability of polyester nanocapsules and nanoparticles: stabilization approaches," *Biomaterials*, vol. 18, No. 19, pp.1305-1310 (1997). [Abstract].

Tian et al., Structural Stability Effects on Adsorption of Bacteriophage T4 Lysozyme to Colloidal Silica, *J. Colloid. Interface Sci.*, vol. 200, pp. 146-154 (1998). [Abstract].

Office Action cited in related U.S. Appl. No. 12/117,982, dated Feb. 2, 2011.

Canadian Office Action cited in related Canadian Patent Application No. 2488499, dated Dec. 16, 2010.

Office Action cited in related U.S. Appl. No. 10/619,539, dated Mar. 15, 2011.

Office Action cited in related U.S. Appl. No. 12/870,722, dated Mar. 29, 2011.

Office Action cited in related U.S. Appl. No. 12/870,745, dated Apr. 1, 2011.

Office Action cited in related U.S. Appl. No. 12/076,247, dated Apr. 14, 2011.

Purohit et al., Inhibition of Tumor Necrosis Factor a-Stimulated Aromatase Activity by Microtubule-Stabilizing Agents, Pacilitaxel and 2-Methoxyestradiol, *Biochemical and Biophysical Research Communications*, vol. 261, Issue 1, Jul. 22, 1999, pp. 214-217.

Arsenault et al., Taxol Involution of Collagen-Indued Arthritis: Ultrastructural Correlation with the Inhibition of Synovitis and Neovascularization Clinical Immunology and Immunopathology, vol. 86, Issue 3, Mar. 1998, pp. 280-289.

Office Action cited in related U.S. Appl. No. 12/320,431, dated Apr. 15, 2011.

Office Action cited in related U.S. Appl. No. 11/928,250, dated Apr. 25, 2011.

Office Action cited in related U.S. Appl. No. 11/928,278, dated Apr. 27, 2011.

Office Action cited in related U.S. Appl. No. 12/928,289, dated Apr. 27, 2011.

Office Action cited in related U.S. Appl. No. 10/667,470, dated May 9, 2011.
Office Action cited by the Examiner in related U.S. Appl. No. 11/367,716, dated May 19, 2011.
Office Action cited by the Examiner in related U.S. Appl. No. 11/980,720, dated May 26, 2011.
Office Action cited by the Examiner in related U.S. Appl. No. 10/677,857, dated Jun. 7, 2011.
Office Action cited by the Examiner in related U.S. Appl. No. 12/483,188, dated Jun. 23, 2011.
Rong-Kun Chang, "Sustained Drug Release from Tablets and Particles Through Coating," Pharmaceutical Dosage Forms, 1990, pp. 199-302.
Office Action dated Sep. 22, 2008, for related U.S. Appl. No. 11/980,586, 14 pgs.
Office Action for related U.S. Appl. No. 10/701,064, dated Feb. 12, 2009, 13 pgs.
Office Action from related U.S. Appl. No. 10/697,716 dated Apr. 15, 2009.
Office Action from related U.S. Appl. No. 10/677,857 dated Jan. 21, 2009.
Office Action cited in related U.S. Appl. No. 12/117,982, dated Jul. 8, 2011.
Office Action cited in related U.S. Appl. No. 09/337,675, dated Aug. 1, 2011.
Office Action cited in related U.S. Appl. No. 12/068,706, dated Jul. 20, 2011.
Damascelli et al., Intraarterial Chemotherapy with Polyoxyethylated Castor Oil Free Paclitaxel, Incorporated in Albumin Nanoparticles (ABI-007) Phase I Study of Patients with Squamous Cell Carcinoma of the Head and Neck and Anal Canal: Preliminary Evidence of Clinical Activity; 2001 Cancer, vol. 92, No. 10, pp. 2592-2602.
Office Action cited in related U.S. Appl. No. 11/928,278, dated Dec. 28, 2009.
Office Action cited in related U.S. Appl. No. 11/928,250, dated Dec. 29, 2009.
Office Action cited in related U.S. Appl. No. 11/928,289, dated Dec. 30, 2009.
Notice of Reasons for Rejections cited in related Japanese Patent Application No. 2003-577857, dated Mar. 29, 2010.
Office Action cited in related U.S. Appl. No. 11/928,250, dated Aug. 4, 2010.
Office Action cited in related U.S. Appl. No. 11/928,278, dated Aug. 4, 2010.
Office Action cited in related U.S. Appl. No. 11/928,289, dated Aug. 3, 2010.
Office Action cited in related U.S. Appl. No. 09/337,675, dated Aug. 30, 2010.
Josefsson et al., "Suppression of Type II Collagen-Induced Arthritis by the Endogenous Estrogen Metabolite 2-Methoxyestradiol," Arthritis & Rheumatism, vol. 40, Issue 1, pp. 154-163 (1997).
Office Action cited in related U.S. Appl. No. 12/870,722, dated Oct. 7, 2010.
Office Action cited in related U.S. Appl. No. 12/870,745, dated Oct. 7, 2010.
Office Action cited in related U.S. Appl. No. 12/076,247, dated Aug. 5, 2010.
Office Action cited in related U.S. Appl. No. 12/320,431, dated Sep. 30, 2010.
Merriam-Webster's Collegiate Dictionary, $10^{th}$ edition, Merriam-Webster Incorp.: Springfield, MA, 1993, pp. 311.
International Search Report for related International Patent Application No. PCT/US2009/036965, completed Jun. 19, 2009.
Written Opinion of the International Searching Authority for related International Patent Application No. PCT/US2009/036965, completed Jun. 19, 2009.
Notice of Rejections for related Japanese Patent Application No. 2003-577857 completed Jul. 6, 2009, 3 pgs.
Notice of Decision to Grant dated Aug. 30, 2010 cited in related Japanese Patent Application No. 2003-565446.
Canadian Office Action dated Mar. 10, 2010, cited in related Canadian Patent Application No. 2,479,665.

European Search Report for related EP Patent Application No. 10179894, dated Nov. 4, 2010.
Office Action cited in related U.S. Appl. No. 10/697,703, dated Nov. 9, 2010.
Office Action cited in related U.S. Appl. No. 11/367,716, dated Nov. 10, 2010.
Office Action cited in related U.S. Appl. No. 12/117,982, dated Dec. 1, 2010.
Matsumoto et al., "Physical Properties of Solid Molecular dispersions of Indomethacin with Poly(vinylpyrrolidone) and Poly(vinylpyrrolidone-co-vinyl-acetate) in Relation to Indomethacin Crystallization," Pharmaceutical Research (1999), vol. 16, No. 11, pp. 1722-1728, XP000987250.
Hülsmann et al., "Melt extrusion—an alternative method for enhancing the dissolution rate of 17β-estradiol hemihydrate," European Journal of Pharmaceutics and Biopharmaceutics (2000), vol. 49, No. 3, pp. 237-242, XP004257163.
Vojnovic et al., "Formulation and evaluation of vinylpyrrolidone/vinylacetate copolymer microspheres and griseofulvin," J. Microencapsulation (1993), vol. 10, No. 1, pp. 89-99, XP000334996.
Bogdanova et al., "Solid Dispersions of Isopropylantipyrin," Labo-Pharma-Probl. Tech. (1984), vol. 32, No. 348, pp. 835-837, XP001097528.
Zingone et al., "Characterization and dissolution study of solid dispersions of theophylline and indomethacin with PVP/VA copolymers," STP Pharma Sciences (1992), vol. 2, No. 2, pp. 186-192, XP002111752.
Office Action for co-pending U.S. Appl. No. 10/697,716, dated Mar. 18, 2008.
Office Action for co-pending U.S. Appl. No. 10/712,259, dated Mar. 17, 2008.
Office Action for co-pending U.S. Appl. No. 10/667,470, dated Mar. 11, 2008.
Office Action for co-pending related U.S. Appl. No. 10/357,514, dated Sep. 21, 2007.
Office Action for related U.S. Appl. No. 11/898,274, dated Oct. 16, 2008, 8 pgs.
Office Action for co-pending related U.S. Appl. No. 09/337,675, dated Nov. 17, 2006.
Office Action for co-pending related U.S. Appl. No. 10/701,064, dated Feb. 7, 2008.
Guidance for Industry, Levothyroxine Sodium Tablets—In Vivo Pharmacokinetic and Bioavailability Studies and In vitro Dissolution Testing, Dec. 2000, pp. 1-8.
Kim et al., "The antihypertensive effect of orally administered nifedipine-loaded nanoparticles in spontaneously hypertensive rats.", British Journal of Pharmacology. 1997, vol. 120, pp. 399-404.
Office Action dated Feb. 12, 2009 for related U.S. Appl. No. 10/701,064, 12 pgs.
J.T. Carstensen, Pharmaceutical Principles of Solid Dosage Forms, pp. 10-11 (Technomic Publishing Co., Inc. (1993).
Schmidt et al., "Incorporation of Polymeric Nanoparticles into Solid Dosage Forms," J. Control Release, 57 (2): 115-125 (1999).
Lindahl et al., "Characterization of Fluids from the Stomach and Proximal Jejunum in Men and Women," Pharm. Res., 14(4): 497-502 (1997).
De Jaeghere et al., "pH-Dependent Dissolving Nano- and Microparticles for Improved Peroral Delivery of a Highly Lipophilic Compound in Dogs," AAPS PharmSci., 3: pp. 1-8 (Feb. 2001).
Office Action dated Sep. 22, 2008 for related U.S. Appl. No. 11/980,586, 14 pgs.
Office Action dated Sep. 18, 2008 for related U.S. Appl. No. 11/979,231, 7 pgs.
Notice of Rejections for Japanese Patent Application No. 2001-529425, dated Jan. 6, 2009, 5 pgs.
Calvo et al., "Development of Positively Charged Colloidal Drug Carriers: Chitosan-Coated Polyester nanocapsules and Submicron-Emulsions," Colloid. Polym. Sci., 275, pp. 46-53 (1997).
Rock et al., "Control of Calcium Carbonate Particle Size and Shape by Precipitation from CTAB/Alcohol/Hexadecane Mixtures," Colloid. Polym. Sci., 275, pp. 893-896 (1997).
Notice of Rejections for Japanese Patent Application No. 2001-583733, dated Jan. 6, 2009., 5 pgs.

Notice of Rejections for Japanese Patent Application No. 2002-528199, dated Oct. 30, 2008, 3 pgs.
Office Action dated Dec. 12, 2008 for related co-pending U.S. Appl. No. 12/078,027, 12 pgs.
Office Action dated Nov. 12, 2008 for related co-pending U.S. Appl. No. 10/667,470, 20 pgs.
Office Action for related U.S. Appl. No. 11/979,231 dated Mar. 13, 2009, 15 pgs.
Office Action cited in related U.S. Appl. No. 11/898,274, dated May 5, 2009.
Office Action cited in related U.S. Appl. No. 10/677,857, dated Jul. 8, 2009.
Office Action cited in related U.S. Appl. No. 10/697,716, dated Apr. 15, 2009.
Notice of Rejections completed Aug. 26, 2009 for related Japanese Patent Application No. 2001-583733.
Office Action cited in related U.S. Appl. No. 10/619,539 dated Sep. 8, 2009.
Office Action cited in related U.S. Appl. No. 11/979,231 dated Sep. 16, 2009.
Office Action cited in related U.S. Appl. No. 10/697,716 dated Sep. 15, 2009.
Office Action cited in related U.S. Appl. No. 11/898,274, dated Oct. 23, 2009.
Office Action cited in related U.S. Appl. No. 10/701,064, dated Nov. 23, 2009.
Office Action cited in related U.S. Appl. No. 11/980,720, dated Oct. 5, 2009.
Office Action for related U.S. Appl. No. 10/697,703, dated Jul. 9, 2009.
Office Action for related U.S. Appl. No. 10/667,470, dated May 19, 2009.
Office Action cited in related U.S. Appl. No. 10/701,064, dated Nov. 14, 2011.
Notice of Reasons for Rejection cited in related Japanese Patent Application No. 2008-227248, dated Oct. 31, 2011.
Written Opinion cited in related Singapore Patent Application No. 201006315-4, dated Dec. 15, 2011.
Office Action cited in related U.S. Appl. No. 12/292,091, dated Jan. 18, 2012.
Czeslik et al., "Effect of Temperature on the Conformation of Lysozyme Adsorbed to Silica Particles," *Phys. Chem. Chem. Phys*., vol. 3, pp. 235-239 (2001).
Abraham, "LXXVII. Some Properties of Egg-White Lysozyme," pp. 622-630 (1939).
Office Action cited in related U.S. Appl. No. 09/337,675, dated Feb. 7, 2012.
Office Action cited in related Canadian Patent Application No. 2,492,488, dated Feb. 28, 2012.

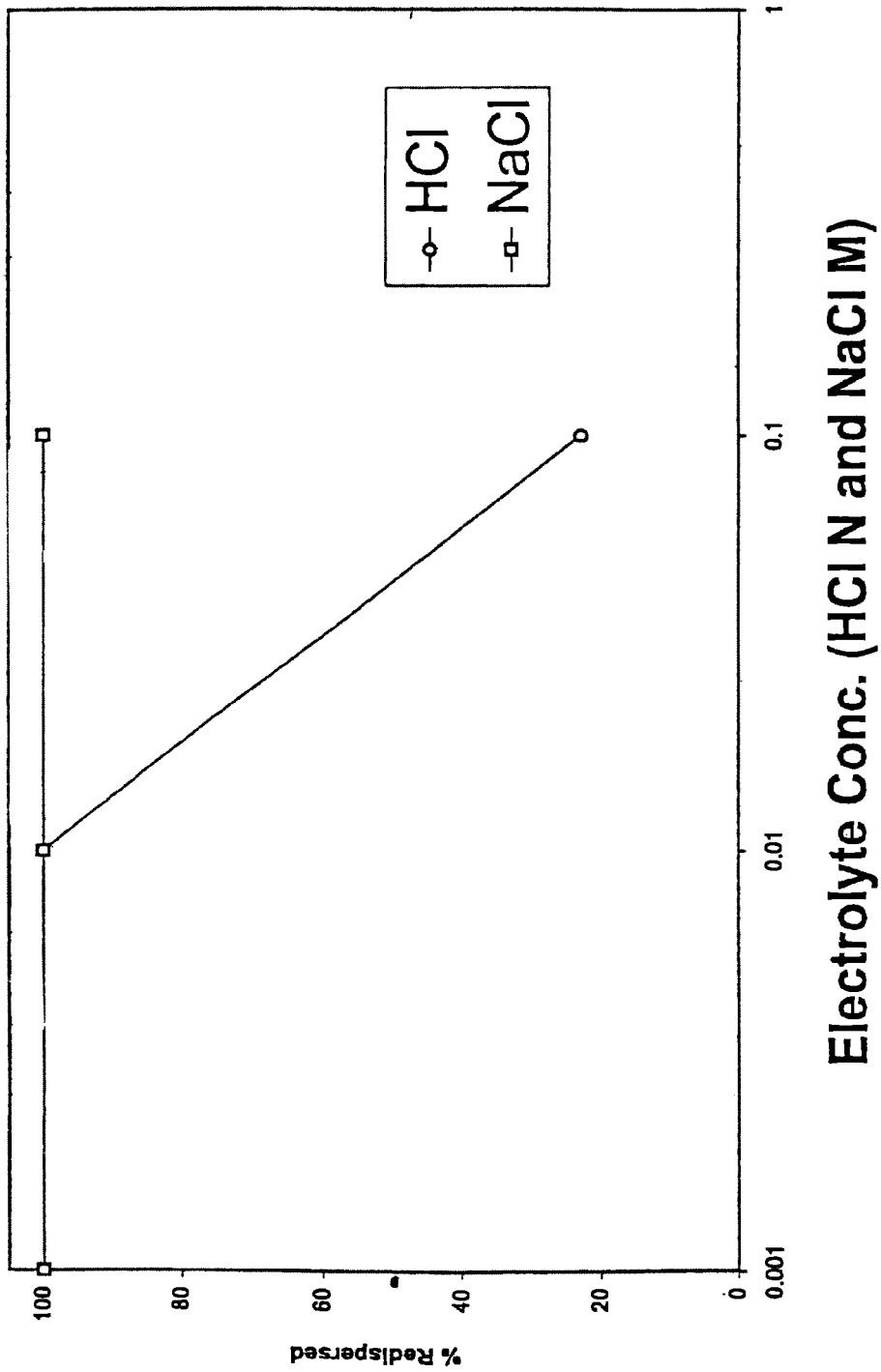

IN VITRO METHODS FOR EVALUATING THE IN VIVO EFFECTIVENESS OF DOSAGE FORMS OF MICROPARTICULATE OR NANOPARTICULATE ACTIVE AGENT COMPOSITIONS

RELATED APPLICATIONS

This application is a continuation of U.S. patent application Ser. No. 11/650,412, filed Jan. 8, 2007, which is a continuation of U.S. patent application Ser. No. 10/323,736, filed on Dec. 20, 2002, now U.S. Pat. No. 7,198,795, which is a continuation-in-part of U.S. patent application Ser. No. 10/075,443, filed on Feb. 15, 2002, now U.S. Pat. No. 6,592,903, which is a continuation of U.S. patent application Ser. No. 09/666,539, filed on Sep. 21, 2000, now U.S. Pat. No. 6,375,986. The contents of these applications are incorporated herein by reference in their entirety.

FIELD OF THE INVENTION

The present invention is directed to in vitro methods of evaluating the in vivo effectiveness of dosage forms of microparticulate or nanoparticulate poorly water-soluble active agent compositions. The methods comprise evaluating the redispersibility of dosage forms of microparticulate or nanoparticulate active agents in a biorelevant aqueous medium that preferably mimics in vivo human physiological conditions.

BACKGROUND OF THE INVENTION

A. Background Regarding Conventional In Vitro Methods for Evaluating the In Vivo Effectiveness of Dosage Forms of Active Agents Active agents are marketed in a wide variety of dosage forms, solid, semi-solid, or liquid dosage formulations, immediate release dosage forms, modified release dosage forms, extended release dosage forms, delayed release dosage forms, pulsatile release dosage forms, controlled release dosage forms, fast melt ("waterless") tablet formulations, dry powders for oral suspension or pulmonary administration, multiparticulates, sprinkles, tablets, capsules and related solid presentations for oral administration, lyophilized formulations, sachets, lozenges, syrups, liquids for injection or oral delivery, etc.

For an active agent to exhibit pharmacological activity, the active agent must dissolve and be absorbed by the patient. If the active agent does not dissolve, absorption will not occur and pharmacological activity will not be achieved. Upon administration of a dosage form, several events must occur prior to dissolution and subsequent absorption of the active agent: (1) the dosage form must disintegrate, (2) disperse into small particles; (3) dissolve in its molecular form (4) followed by absorption. If an active agent is not dispersed sufficiently it will not be dissolved readily and consequently will pass through the gastrointestinal tract of the patient, resulting in low bioavailability of the administered active agent.

Conventional in vitro analytical methodologies for evaluating the in vivo effectiveness of poorly water-soluble active agents attempt to assess product quality by measuring the rate and extent of active agent dissolution in an aqueous medium, and generally in the presence of surfactants or cosolvents. See e.g., Umesh V. Banakar, *Pharmaceutical Dissolution Testing, Drugs and Pharmaceutical Sciences*, Vol. 49 (1992). Such aggressive solubilizing agents can decrease the sensitivity of the analytical test. Moreover, such dissolution tests are conducted in media which are generally not reflective of in vivo human physiological conditions and do not measure the dosage form's redispersibility qualities. See e.g., J. T. Carstensen, *Pharmaceutical Principles of Solid Dosage Forms*, pp. 10-11 (Technomic Publishing Co., Inc. (1993); Schmidt et al., "Incorporation of Polymeric Nanoparticles into Solid Dosage Forms," *J. Control Release*, 57 (2): 115-25 (1999). See also Volker Bühler, *Generic Drug Formulations*, Section 4.3 (Fine Chemicals, $2^{nd}$ Edition, 1998). See De Jaeghere et al., "pH-Dependent Dissolving Nano- and Microparticles for Improved Peroral Delivery of a Highly Lipophilic Compound in Dogs," *AAPS PharmSci.*, 3:8 (February 2001).

Following disintegration, the next step in making an active agent bioavailable from a nanoparticulate or microparticulate dosage form is the redispersibility of the formulation back to the original nanoparticulate or microparticulate active agent particle size present before the active agent was formulated into a dosage form. Therefore, the ability of a method to quantitate that part of the process is at least as important as the actual dissolution of the active agent. In fact, this part of the process is more relevant for poorly soluble components than the last step of the process in predicting in vivo bioavailability.

B. Background Regarding Nanoparticulate Compositions

Nanoparticulate compositions, first described in U.S. Pat. No. 5,145,684 ("the '684 patent"), are particles consisting of a poorly soluble active agent having adsorbed onto the surface thereof a non-crosslinked surface stabilizer. The '684 patent also describes methods of making such nanoparticulate compositions. Nanoparticulate compositions are desirable because with a decrease in particle size, and a consequent increase in surface area, a composition can exhibit superior bioavailability.

Redispersibility properties of a nanoparticulate based dosage form are especially important, since when the dosage form of a nanoparticulate active agent does not suitably redisperse following administration, the benefits of formulating the active agent into nanoparticles may be compromised or altogether lost. This is because in the absence of redispersibility the dosage form produces clumps or large aggregates of particles, and not discrete nanoparticles of active agent.

Methods of making nanoparticulate compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described, for example, in U.S. Pat. Nos. 5,298,262 for "Use of Ionic Cloud Point Modifiers to Prevent Particle Aggregation During Sterilization;" 5,302,401 for "Method to Reduce Particle Size Growth During Lyophilization;" 5,318,767 for "X-Ray Contrast Compositions Useful in Medical Imaging;" 5,326,552 for "Novel Formulation For Nanoparticulate X-Ray Blood Pool Contrast Agents Using High Molecular Weight Non-ionic Surfactants;" 5,328,404 for "Method of X-Ray Imaging Using Iodinated Aromatic Propanedioates;" 5,336,507 for "Use of Charged Phospholipids to Reduce Nanoparticle Aggregation;" 5,340,564 for "Formulations Comprising Olin 10-G to Prevent Particle Aggregation and Increase Stability;" 5,346,702 for "Use of Non-Ionic Cloud Point Modifiers to Minimize Nanoparticulate Aggregation During Sterilization;" 5,349,957 for "Preparation and Magnetic Properties of Very Small Magnetic-Dextran Particles;" 5,352,459 for "Use of Purified Surface Modifiers to Prevent Particle Aggregation During Sterilization;" 5,399,363 and 5,494,683, both for "Surface Modified Anticancer Nanoparticles;" 5,401,492 for "Water Insoluble Non-Magnetic Manganese Particles as Magnetic Resonance Enhancement Agents;" 5,429,824 for "Use of Tyloxapol as a Nanoparticulate Stabilizer;" 5,447,710 for "Method for Making Nanoparticulate X-Ray Blood Pool Contrast Agents Using High Molecular Weight Non-ionic Surfactants;" 5,451,393 for "X-Ray Contrast Compositions Useful in Medical Imaging;" 5,466,440 for "Formulations of Oral Gastrointestinal Diagnostic X-Ray Contrast Agents in Combination with Pharmaceutically Acceptable Clays;" 5,470,583 for "Method of Preparing Nanoparticle Compositions Containing Charged Phospholipids to Reduce Aggregation;" 5,472,683 for "Nanoparticulate Diagnostic Mixed Carbamic Anhydrides as X-Ray Contrast Agents for Blood Pool and Lymphatic System Imaging;" 5,500,204 for "Nanoparticulate Diagnostic Dimers as X-Ray Contrast Agents for Blood Pool and Lymphatic System Imaging;" 5,518,738 for "Nanoparticulate NSAID Formulations;" 5,521,218 for "Nanoparticulate Iododipamide Derivatives for Use as X-Ray Contrast Agents;" 5,525,328 for "Nanoparticulate Diagnostic Diatrizoxy Ester X-Ray Contrast Agents for Blood Pool and Lymphatic System Imaging;" 5,543,133 for "Process of Preparing X-Ray Contrast Compositions Containing Nanoparticles;" 5,552,160 for "Surface Modified NSAID Nanoparticles;" 5,560,931 for "Formulations of Compounds as Nanoparticulate Dispersions in Digestible Oils or Fatty Acids;" 5,565,188 for "Polyalkylene Block Copolymers as Surface Modifiers for Nanoparticles;" 5,569,448 for "Sulfated Non-ionic Block Copolymer Surfactant as Stabilizer Coatings for Nanoparticle Compositions;" 5,571,536 for "Formulations of Compounds as Nanoparticulate Dispersions in Digestible Oils or Fatty Acids;" 5,573,749 for "Nanoparticulate Diagnostic Mixed Carboxylic Anhydrides as X-Ray Contrast Agents for Blood Pool and Lymphatic System Imaging;" 5,573,750 for "Diagnostic Imaging X-Ray Contrast Agents;" 5,573,783 for "Redispersible Nanoparticulate Film Matrices With Protective Overcoats;" 5,580,579 for "Site-specific Adhesion Within the GI Tract Using Nanoparticles Stabilized by High Molecular Weight, Linear Poly(ethylene Oxide) Polymers;" 5,585,108 for "Formulations of Oral Gastrointestinal Therapeutic Agents in Combination with Pharmaceutically Acceptable Clays;" 5,587,143 for "Butylene Oxide-Ethylene Oxide Block Copolymers Surfactants as Stabilizer Coatings for Nanoparticulate Compositions;" 5,591,456 for "Milled Naproxen with Hydroxypropyl Cellulose as Dispersion Stabilizer;" 5,593,657 for "Novel Barium Salt Formulations Stabilized by Non-ionic and Anionic Stabilizers;" 5,622,938 for "Sugar Based Surfactant for Nanocrystals;" 5,628,981 for "Improved Formulations of Oral Gastrointestinal Diagnostic X-Ray Contrast Agents and Oral Gastrointestinal Therapeutic Agents;" 5,643,552 for "Nanoparticulate Diagnostic Mixed Carbonic Anhydrides as X-Ray Contrast Agents for Blood Pool and Lymphatic System Imaging;" 5,718,388 for "Continuous Method of Grinding Pharmaceutical Substances;" 5,718,919 for "Nanoparticles Containing the R(−)Enantiomer of Ibuprofen;" 5,747,001 for "Aerosols Containing Beclomethasone Nanoparticle Dispersions;" 5,834,025 for "Reduction of Intravenously Administered Nanoparticulate Formulation Induced Adverse Physiological Reactions;" 6,045,829 "Nanocrystalline Formulations of Human Immunodeficiency Virus (HIV) Protease Inhibitors Using Cellulosic Surface Stabilizers;" 6,068,858 for "Methods of Making Nanocrystalline Formulations of Human Immunodeficiency Virus (HIV) Protease Inhibitors Using Cellulosic Surface Stabilizers;" 6,153,225 for "Injectable Formulations of Nanoparticulate Naproxen;" 6,165,506 for "New Solid Dose Form of Nanoparticulate Naproxen;" 6,221,400 for "Methods of Treating Mammals Using Nanocrystalline Formulations of Human Immunodeficiency Virus (HIV) Protease Inhibitors;" 6,264,922 for "Nebulized Aerosols Containing Nanoparticle Dispersions;" 6,267,989 for "Methods for Preventing Crystal Growth and Particle Aggregation in Nanoparticle Compositions;" 6,270,806 for "Use of PEG-Derivatized Lipids as Surface Stabilizers for Nanoparticulate Compositions;" 6,316,029 for "Rapidly Disintegrating Solid Oral Dosage Form," 6,375,986 for "Solid Dose Nanoparticulate Compositions Comprising a Synergistic Combination of a Polymeric Surface Stabilizer and Dioctyl Sodium Sulfosuccinate;" 6,428,814 for "Bioadhesive nanoparticulate compositions having cationic surface stabilizers;" and 6,432,381 for "Methods for targeting drug delivery to the upper and/or lower gastrointestinal tract," all of which are specifically incorporated by reference. In addition, U.S. Patent Application No. 20020012675 A1, published on Jan. 31, 2002, for "Controlled Release Nanoparticulate Compositions," describes nanoparticulate compositions, and is specifically incorporated by reference.

Amorphous small particle compositions are described, for example, in U.S. Pat. Nos. 4,783,484 for "Particulate Composition and Use Thereof as Antimicrobial Agent;" 4,826,689 for "Method for Making Uniformly Sized Particles from Water-Insoluble Organic Compounds;" 4,997,454 for "Method for Making Uniformly-Sized Particles From Insoluble Compounds;" 5,741,522 for "Ultrasmall, Non-aggregated Porous Particles of Uniform Size for Entrapping Gas Bubbles Within and Methods;" and 5,776,496, for "Ultrasmall Porous Particles for Enhancing Ultrasound Back Scatter."

There is a need in the art for effective in vitro methods of evaluating the in vivo effectiveness of dosage forms of microparticulate and nanoparticulate poorly water-soluble active agents. The present invention satisfies this need.

SUMMARY OF THE INVENTION

The present invention is directed to the surprising discovery that the in vivo effectiveness of dosage forms of nanoparticulate and microparticulate poorly water-soluble active agents can be reliably predicted by utilizing an in vitro redispersibility test. The redispersibility test employs biorelevant aqueous media that mimic human physiological conditions, rather than aggressive, surfactant-enriched or cosolvent-enriched media that facilitate rapid and complete dissolution of the active pharmaceutical agent.

The redispersibility test of the invention is a quantitative measure of the ability of a formulation to regenerate particle sizes that are optimum in vivo. Such regenerated particle sizes are generally similar to the primary active agent particle size present prior to formulating the active agent into a dosage form. For example, if a nanoparticulate active agent dispersion is used to make the dosage form, then the primary active agent particle size is that present in the dispersion. The test employs biorelevant aqueous media which mimic in vivo human physiological conditions, such as the ionic strength and pH found in vivo. Such biorelevant aqueous media can be electrolyte solutions, such as HCl or NaCl solutions, or solutions of other salts and acids, or combinations thereof, which have the desired biorelevant characteristics.

The method is a dramatic improvement over prior art methods, as the conventional in vitro method of measuring dissolution of a dosage form in a surfactant-enriched or cosolvent-enriched medium may have no correlation with redispersibility observed under in vivo human physiological conditions.

Also provided by the invention are dosage forms selected by the method of the invention, and methods of using such dosage forms.

Both the foregoing general description and the following detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE FIGURES

FIG. 2: Shows the percent redispersibility in electrolyte solutions, as a function of electrolyte concentration, for a spray dried nanoparticulate MAP kinase inhibitor composition.

DETAILED DESCRIPTION OF THE INVENTION

Figure 1:
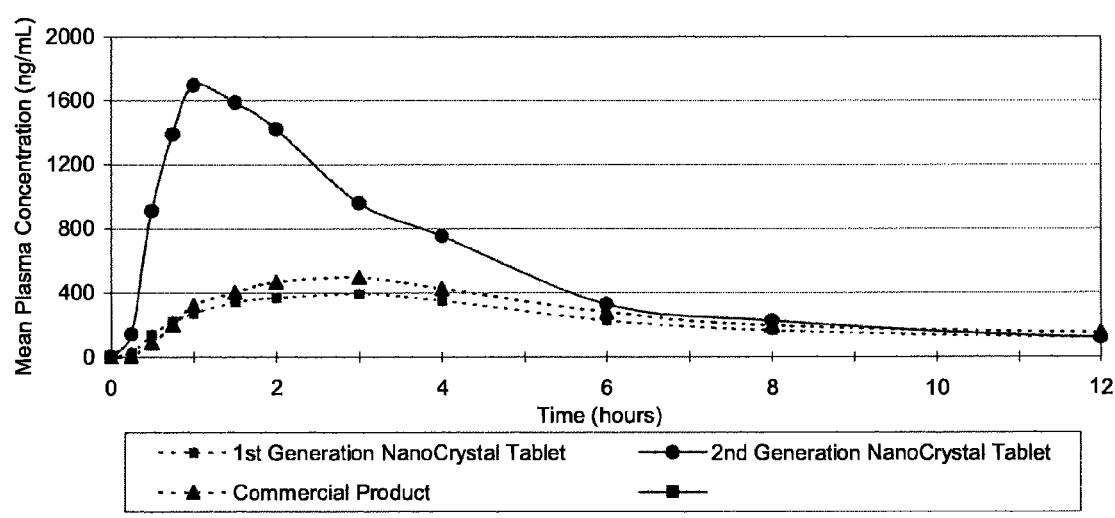
FIG. 1: Shows the mean pharmacokinetic profiles in fasted human volunteers upon oral administration of a single 200-mg dose of two nanoparticulate active agent tablet formulations and a commercial capsule formulation (reference product)

One frequent problem associated with prior art poorly water-soluble active agent compositions was that upon administration to a patient, such as a human or animal, the active agent composition would not redisperse in vivo to a particle size having optimum characteristics for in vivo performance. As a lack of redispersibility upon administration may result in an ineffective dosage form, the ability to predict in vivo redispersibility is critical to successful dosage form design.

Poor redispersibility is particularly problematic for nanoparticulate active agent compositions, for when the nanoparticulate active agent dosage form fails to redisperse upon administration, the dosage form may lose the benefits afforded by formulating the active agent into a nanoparticulate particle size. This is because nanoparticulate active agent compositions benefit from the small particle size of the active agent; if the active agent does not redisperse into the small particle sizes upon administration, then "clumps" or agglomerated active agent particles are formed, owing to the extremely high surface free energy of the nanoparticulate system and the thermodynamic driving force to achieve an overall reduction in free energy. With the formation of such agglomerated particles, the bioavailability of the dosage form may fall well below that observed with the liquid dispersion form of the nanoparticulate active agent.

Similar benefits can also be obtained by designing a microparticulate dosage form using the method of the invention, as regardless of the particle size of the component active agent, faster and more complete dissolution of a microparticulate active agent dosage form is desirable.

The invention is applicable to in vitro methods for evaluating a wide variety of dosage forms, such as solid, semisolid, or liquid dosage formulations, immediate release dosage forms, modified release dosage forms, extended release dosage forms, delayed release dosage forms, pulsatile release dosage forms, controlled release dosage forms, fast melt ("waterless") tablet formulations, dry powders, such as those for oral suspension or pulmonary or nasal administration, multiparticulates, sprinkles, tablets, capsules and related solid presentations for oral administration, lyophilized formulations, sachets, lozenges, syrups, liquids for injection or oral delivery, etc. In sum, any dosage form can be evaluated by the method of the invention, including but not limited to dosage forms intended for oral, pulmonary, nasal, parenteral, rectal, local, or buccal delivery.

The methods of the invention are directed to in vitro techniques capable of quantifying the rate and extent of active agent redispersibility upon introduction of particulate poorly water-soluble active agent dosage forms into biorelevant aqueous media. Such biorelevant aqueous media can be any aqueous media that exhibit the desired ionic strength and pH, which form the basis for the biorelevance of the media. The desired pH and ionic strength are those that are representative of physiological conditions found in the human body. Such biorelevant aqueous media can be, for example, aqueous electrolyte solutions or aqueous solutions of any salt, acid, or base, or a combination thereof, which exhibit the desired pH and ionic strength.

Biorelevant pH is well known in the art. For example, in the stomach, the pH ranges from slightly less than 2 (but typically greater than 1) up to 4 or 5. In the small intestine the pH can range from 4 to 6, and in the colon it can range from 6 to 8. Biorelevant ionic strength is also well known in the art. Fasted state gastric fluid has an ionic strength of about 0.1M while fasted state intestinal fluid has an ionic strength of about 0.14. See e.g., Lindahl et al., "Characterization of Fluids from the Stomach and Proximal Jejunum in Men and Women," *Pharm. Res.*, 14 (4): 497-502 (1997).

It is believed that the pH and ionic strength of the test solution is more critical than the specific chemical content. Accordingly, appropriate pH and ionic strength values can be obtained through numerous combinations of strong acids, strong bases, salts, single or multiple conjugate acid-base pairs (i.e., weak acids and corresponding salts of that acid), monoprotic and polyprotic electrolytes, etc.

Representative electrolyte solutions can be, but are not limited to, HCl solutions, ranging in concentration from about 0.001 to about 0.1 M, and NaCl solutions, ranging in concentration from about 0.001 to about 0.1 M, and mixtures thereof. For example, electrolyte solutions can be, but are not limited to, about 0.1 M HCl or less, about 0.01 M HCl or less, about 0.001 M HCl or less, about 0.1 M NaCl or less, about 0.01 M NaCl or less, about 0.001 M NaCl or less, and mixtures thereof. Of these electrolyte solutions, 0.01 M HCl and/or 0.1 M NaCl, are most representative of fasted human physiological conditions, owing to the pH and ionic strength conditions of the proximal gastrointestinal tract.

Electrolyte concentrations of 0.001 M HCl, 0.01 M HCl, and 0.1 M HCl correspond to pH 3, pH 2, and pH 1, respectively. Thus, a 0.01 M HCl solution simulates typical acidic conditions found in the stomach. A solution of 0.1 M NaCl provides a reasonable approximation of the ionic strength conditions found throughout the body, including the gastrointestinal fluids, although concentrations higher than 0.1 M may be employed to simulate fed conditions within the human GI tract.

Exemplary solutions of salts, acids, bases or combinations thereof, which exhibit the desired pH and ionic strength, include but are not limited to phosphoric acid/phosphate salts+sodium, potassium and calcium salts of chloride, acetic acid/acetate salts+sodium, potassium and calcium salts of chloride, carbonic acid/bicarbonate salts+sodium, potassium and calcium salts of chloride, and citric acid/citrate salts+sodium, potassium and calcium salts of chloride.

In an exemplary method, aliquots of biorelevant aqueous media from vessels containing the dosage form to be tested are removed at appropriate time points and the amount of redispersed active agent is quantitated by UV analysis at an appropriate wavelength using a standard. Other suitable assay methods such as chromatography can also be utilized in the methods of the invention. Confirmation of the particle size of the active agent can be made using, e.g., a particle size distribution analyzer. In cases where all components except the active are completely water-soluble, the redispersibility process can be monitored exclusively by particle size analysis. Conventional USP dissolution apparatus can also be utilized in the methods of the invention.

Assay methods for nanoparticulate materials can be based on quantitation of all active agent in the sample after removal of larger material using an appropriate filter technique. Alternatively, in situ spectroscopic detection techniques sensitive to the size and/or concentration of nanoparticulate active agents can be employed. A combination of multivariate analysis techniques and various forms of multi-wavelength molecular spectroscopy (ultraviolet (UV), visible (VIS), near infrared (NIR) and/or Raman resonance) can be used for simultaneous and rapid evaluation of both mean particle size and concentration of the nanoparticulate active agent.

In the methods of the invention, a dosage form of a nanoparticulate active agent is expected to exhibit optimum in vivo performance when upon reconstitution in a biorelevant aqueous medium, the dosage form redisperses such that the particle size distribution of the redispersed nanoparticulate active agent particles resembles the distribution of the particles prior to incorporation into the dosage form. For example, such a prior particle size can be the particle size of the active agent present in a nanoparticulate active agent dispersion used to manufacture the dosage form.

In the methods of the invention, a dosage form of a nanoparticulate active agent is expected to exhibit optimum in vivo performance when upon reconstitution in a biorelevant aqueous medium, the dosage form redisperses such that:
 (a) if prior to incorporation into a dosage form the active agent has an effective average particle size of less than about 2 microns, then following redispersibility 90% of the active agent particles have a particle size of less than about 10 microns,
 (b) if prior to incorporation into a dosage form the active agent has an effective average particle size of less than about 1 micron, then following redispersibility 90% of the active agent particles have a particle size of less than about 5 microns,
 (c) if prior to incorporation into a dosage form the active agent has an effective average particle size of less than about 800 nm, then following redispersibility 90% of the active agent particles have a particle size of less than about 4 microns,
 (d) if prior to incorporation into a dosage form the active agent has an effective average particle size of less than about 600 nm, then following redispersibility 90% of the active agent particles have a particle size of less than about 3 microns,
 (e) if prior to incorporation into a dosage form the active agent has an effective average particle size of less than about 400 nm, then following redispersibility 90% of the active agent particles have a particle size of less than about 2 microns, and
 (f) if prior to incorporation into a dosage form the active agent has an effective average particle size of less than about 200 nm, then following redispersibility 90% of the active agent particles have a particle size of less than about 1 micron.

Similarly, in the methods of the invention, a dosage form of a microparticulate active agent is expected to exhibit optimum in vivo performance when, upon reconstitution in a biorelevant aqueous medium, the dosage form redisperses such that the particle size distribution of the redispersed microparticulate active agent particles resembles the distribution of the particles in the original microparticulate active agent used to manufacture the dosage form.

The techniques of the present invention differ considerably from conventional analytical methodologies for poorly water-soluble active agents, which attempt to assess product quality by measuring the rate and extent of active agent dissolution, generally in the presence of surfactants or cosolvents. In contrast to prior methods of measuring dissolution, the methods of the present invention provide for direct physical measurement of an active agent's exposed surface area, i.e., its redispersibility. Moreover, this measurement is in the absence of extraneous solubilizing agents that could otherwise decrease the sensitivity of the analytical test.

The in vitro redispersibility methods of the invention have been implemented successfully to select a dosage form for optimal in vivo performance over the dosage form which would have been selected relying on conventional dissolution techniques. Specifically, Example 1, below, shows the results of a comparison between the in vivo performance of a conventional solid dose microparticulate active agent, a first generation solid dose nanoparticulate active agent, developed using conventional dissolution methods, and a second generation solid dose nanoparticulate active agent, developed using the redispersibility methods of the invention (the active agent is the same for all three compositions).

The data of Example 1, shown in FIG. 1, depict mean pharmacokinetic profiles in human volunteers following oral administration of single 200-mg doses of two nanoparticulate active agent tablet formulations and a commercial capsule formulation (reference product). The primary goal of the study was to demonstrate an increased rate of active agent absorption upon oral administration (i.e., faster onset of action).

The plasma level the plasma level at the 3-hour time point for the commercial product was 495.04 ng/mL. Interpolating linearly between the 0.25 and 0.50 hour time points for the nanoparticulate formulation indicates that a plasma level of 495 ng/mL is reached at 0.37 hours. This is about ⅛th of the time it takes to reach the same level with the commercial formulation, or about 12% of the time it takes to reach the same level with the commercial formulation. Thus, the results show that the "second generation" nanoparticulate active agent tablet formulation, developed using the redispersibility methodology of the invention, achieved a reduction in time to onset of approximately 88% (based upon time required to achieve maximum blood levels of ca. 500 ng/mL for the commercial product) and further resulted in an unexpected increase in bioavailability of approximately 50%.

Surprisingly, the "first generation" nanoparticulate active agent tablet formulation, developed using conventional dissolution methodology, failed to improve time to onset or increase the bioavailability of the active agent. Thus, particle size of the originally milled dispersion alone cannot predict the in vivo efficacy of a dosage form. Rather, in vivo redispersibility of the dosage form is critical to in vivo efficacy.

Accordingly, the redispersibility methods of the invention are powerful tools for ensuring product quality throughout all stages of development, scale-up, and product transfer to commercial manufacturing sites.

Also provided by the invention are dosage forms selected by the method of the invention, and methods of using such dosage forms. Such dosage forms include, but are not limited to, solid, semi-solid, or liquid dosage formulations, immediate release dosage forms, modified release dosage forms, extended release dosage forms, delayed release dosage forms, pulsatile release dosage forms, controlled release dosage forms, fast melt ("waterless") tablet formulations, dry powders, such as those for oral suspension or pulmonary or nasal administration, multiparticulates, sprinkles, tablets, capsules and related solid presentations for oral administration, lyophilized formulations, sachets, lozenges, syrups, liquids for injection or oral delivery, etc. In sum, any dosage form can be designed using the methodology of the invention, including but not limited to dosage forms intended for oral, pulmonary, nasal, parenteral, rectal, local, or buccal delivery.

The dosage forms identified using the method of the invention can be used to treat any human or animal in need.

A. Compositions to be Evaluated in a Method of the Invention

Any dosage form containing poorly soluble active ingredients can be evaluated according to the methods of the invention. The compositions to be evaluated comprise at least one poorly water-soluble microparticulate active agent, poorly water-soluble nanoparticulate active agent, or a combination thereof. By "poorly water-soluble" it is meant that the active agent has a solubility in water of less than about 30 mg/ml, less than about 10 mg/mL, or less than about 1 mg/mL at ambient temperature and pressure and at about pH 7.

As used in the present invention, a "nanoparticulate" active agent has an effective average particle size of less than about 2 microns, and a microparticulate active agent has an effective average particle size of greater than about 2 microns. Particle size is defined in more detail below.

Based upon overall physical properties and generalized appearance, a dosage form of a nanoparticulate active agent is not readily distinguishable from a traditional microparticulate active agent dosage form. Functionally, however, the performance of the nanoparticulate active agent dosage form is enhanced considerably, due to the increased rate of presentation of active agent to the absorbing surfaces of the gastrointestinal tract.

Proven therapeutic benefits of dosage forms of nanoparticulate active agents include, but are not limited to: faster onset of action, increased bioavailability, reduced fed/fasted variable absorption (i.e., "food effect"), and improved dose proportionality. Other potential advantages of nanoparticulate active agent technology relevant to the development and manufacture of pharmaceutical dosage forms include: improved chemical stability of the active agent, improved physical stability and performance stability of the dosage form, enhanced appearance (i.e., elegant, compact presentation), improved processability and reduced impact of lot-to-lot variability in active agent, rapid development, and predictable performance throughout product development, scale-up, and transfer to commercial manufacturing site.

1. Active Agents

The active agent may be present either substantially in the form of one optically pure enantiomer or as a mixture, racemic or otherwise, of enantiomers. In addition, the active agent exists as a discrete, crystalline phase, as an amorphous phase, a semi-crystalline phase, a semi-amorphous phase, or a combination thereof.

Exemplary active agents can be therapeutic or diagnostic agents, collectively referred to as "drugs". A therapeutic agent can be a pharmaceutical agent, including biologics such as proteins, peptides, and nucleotides, or a diagnostic agent, such as a contrast agent, including x-ray contrast agents.

The active agent can be selected from a variety of known classes of drugs, including, for example, COX-2 inhibitors, retinoids, anticancer agents, NSAIDS, proteins, peptides, nucleotides, anti-obesity drugs, nutraceuticals, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (e.g., hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, xanthines, alpha-hydroxy formulations, cystic-fibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis and other infections of the lung, and respiratory illness therapies associated with acquired immune deficiency syndrome.

Exemplary nutraceuticals and dietary supplements are disclosed, for example, in Roberts et al., *Nutraceuticals: The Complete Encyclopedia of Supplements, Herbs, Vitamins, and Healing Foods* (American Nutraceutical Association, 2001), which is specifically incorporated by reference. A nutraceutical or dietary supplement, also known as phytochemicals or functional foods, is generally any one of a class of dietary supplements, vitamins, minerals, herbs, or healing foods that have medical or pharmaceutical effects on the body. Exemplary nutraceuticals or dietary supplements include, but are not limited to, lutein, folic acid, fatty acids (e.g., DHA and ARA), fruit and vegetable extracts, vitamin and mineral supplements, phosphatidylserine, lipoic acid, melatonin, glucosamine/chondroitin, Aloe Vera, Guggul, glutamine, amino acids (e.g., iso-leucine, leucine, lysine, methionine, phenylanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bio-engineered foods genetically engineered to have a desired property, also known as "pharmafoods."

The active agents are commercially available and/or can be prepared by techniques known in the art.

2. Surface Stabilizers for Nanoparticulate Active Agents

If the active agent has a nanoparticulate particle size prior to incorporation into a dosage form, with "nanoparticulate" being defined as an effective average particle size of less than about 2 microns, then the active agent generally will have at least one surface stabilizer adsorbed on the surface of the active agent.

Surface stabilizers useful herein physically adhere on the surface of the nanoparticulate active agent but do not chemically react with the active agent particles or itself. Individually adsorbed molecules of the surface stabilizer are essentially free of intermolecular cross-linkages.

Exemplary useful surface stabilizers include, but are not limited to, known organic and inorganic pharmaceutical excipients. Such excipients include various polymers, low molecular weight oligomers, natural products, and surfactants. Preferred surface stabilizers include nonionic and ionic surfactants, including anionic and cationic surfactants. Combinations of more than one surface stabilizer can be used in the invention.

Representative examples of surface stabilizers include hydroxypropyl methylcellulose, hydroxypropylcellulose, polyvinylpyrrolidone, random copolymers of vinyl pyrrolidone and vinyl acetate, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropylmethylcellulose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), Tritons X-200®, which is an alkyl aryl polyether sulfonate (Dow); Crodestas F-110®, which is a mixture of sucrose stearate and sucrose distearate (Croda Inc.); p-isononylphenoxypoly-(glycidol), also known as Olin-lOG® or Surfactant 10-G® (Olin Chemicals, Stamford, Conn.); Crodestas SL-40® (Croda, Inc.); and SA9OHCO, which is $C_{18}H_{37}CH_2C(O)N(CH_3)$—$CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, PEG-vitamin E, lysozyme, and the like.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl($C_{12-18}$) dimethylbenzyl ammonium chloride, N-alkyl($C_{14-18}$) dimethyl-benzyl ammonium chloride, N-tetradecylidmethylbenzyl ammonium chloride monohydrate, dimethyl didecyl ammonium chloride, N-alkyl and ($C_{12-14}$)dimethyl 1-napthylmethyl ammonium chloride, trimethylammonium halide, alkyl-trimethylammonium salts and di alkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$)dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctyl ammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Particularly preferred nonpolymeric primary stabilizers are any nonpolymeric compound, such benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:

(i) none of $R_1$-$R_4$ are $CH_3$;
(ii) one of $R_1$-$R_4$ is $CH_3$;
(iii) three of $R_1$-$R_4$ are $CH_3$;
(iv) all of $R_1$-$R_4$ are $CH_3$;
(v) two of $R_1$-$R_4$ are $CH_3$, one of $R_1$-$R_4$ is $C_6H_5CH_2$, and one of $R_1$-$R_4$ is an alkyl chain of seven carbon atoms or less;
(vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
(vii) two of $R_1$-$R_4$ are $CH_3$ and one of $R_1$-$R_4$ is the group $C_6H_5(CH_2)_n$, where n>1;
(viii) two of $R_1$-$R_4$ are $CH_3$, one of $R_1$-$R_4$ is $C_6H_5CH_2$, and one of $R_1$-$R_4$ comprises at least one heteroatom;
(ix) two of $R_1$-$R_4$ are $CH_3$, one of $R_1$-$R_4$ is $C_6H_5CH_2$, and one of $R_1$-$R_4$ comprises at least one halogen;
(x) two of $R_1$-$R_4$ are $CH_3$, one of $R_1$-$R_4$ is $C_6H_5CH_2$, and one of $R_1$-$R_4$ comprises at least one cyclic fragment;
(xi) two of $R_1$-$R_4$ are $CH_3$ and one of $R_1$-$R_4$ is a phenyl ring; or
(xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference. The surface stabilizers are commercially available and/or can be prepared by techniques known in the art.

3. Microparticulate and Nanoparticulate
Particle Size of the Poorly Water-Soluble Active Agent As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifugation.

By "an effective average particle size of less than about 2 microns" it is meant that the arithmetic mean of the weight distribution (the weight fraction as a function of particle size) is less than about 2 microns when measured by the above techniques.

Similarly, by "an effective average particle size of greater than about 2 microns" it is meant that at the arithmetic mean of the weight distribution of the active agent particles is greater than about 2 microns when measured by the above techniques.

If the active agent has a nanoparticulate particle size, then at least about 50%, about 70%, about 90%, or about 95% of the active agent particles can have an average particle size of less than the effective average, i.e., less than about 2 microns.

In addition, in other embodiments of the invention, the effective average particle size of the nanoparticulate active agent particles can be less than about 1500 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 100 nm, less than about 75 nm, or less than about 50 nm.

If the active agent has a microparticulate particle size, the effective average particle size of the microparticulate active agent composition can be greater than about 2 microns, greater than about 5 microns, greater than about 10 microns, greater than about 15 microns, and greater than about 20 microns.

4. Concentration of Nanoparticulate
Active Agent and Surface Stabilizer

If the active agent is in a nanoparticulate particle size, then the active agent has one or more surface stabilizers adsorbed onto the surface of the agent. The relative amount of active agent and one or more surface stabilizers can vary widely. The optimal amount of the surface stabilizer(s) can depend, for example, upon the particular active agent selected, the equivalent hydrophilic lipophilic balance (HLB) of the active agent, the melting point, cloud point, and water solubility of the surface stabilizer, and the surface tension of water solutions of the stabilizer, etc.

The concentration of at least one active agent can vary from about 99.5% to about 0.001%, from about 95% to about 0.1%, or from about 90% to about 0.5%, by weight, based on the total combined weight of the at least one active agent and at least one surface stabilizer, not including other excipients.

The concentration of at least one surface stabilizer can vary from about 0.5% to about 99.999%, from about 5% to about 99.9%, and from about 10% to about 99.5%, by weight, based on the total combined dry weight of at least one active agent and at least one surface stabilizer, not including other excipients.

B. Methods of Making Nanoparticulate Formulations

Nanoparticulate active agent compositions can be made using methods known in the art such as, for example, milling, homogenization, and precipitation techniques.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

In the examples that follow, the value for D50 is the particle size below which 50% of the active agent particles fall. Similarly, D90 is the particle size below which 90% of the active agent particles fall.

Example 1

The purpose of this example was to compare the in vivo performance of a conventional solid dose microparticulate active agent, a first generation solid dose nanoparticulate active agent, and a second generation solid dose nanoparticulate active agent developed using the redispersibility methods of the invention. The active agent is poorly water-soluble.

Human volunteers were orally administered a single 200-mg dose of a conventional solid dose microparticulate active agent, a first generation solid dose nanoparticulate active agent, and a second generation solid dose nanoparticulate active agent. FIG. 1 shows the mean pharmacokinetic profiles of each dosage form following administration. Greater plasma levels of active agent correspond to greater bioavailability of administered active agent.

Surprisingly, the first generation solid dose nanoparticulate active agent dosage form exhibited minimal, if any, increased bioavailability or time to onset over the conventional microparticulate dosage form while the in vitro dissolution data indicated that a superior performance over the conventional dosage form should be expected.

Only the "second generation" nanoparticulate active agent tablet formulation, developed using the redispersibility methodology of the invention, achieved a reduction in time to onset of approximately 90% (based upon time required to achieve maximum blood levels of ca. 500 ng/mL for the commercial product) and further resulted in an unexpected increase in bioavailability of approximately 50%.

The results of this example demonstrate that active agent particle size in the solid dose form alone will not determine the in vivo effectiveness of an orally administered solid dosage form. Rather, redispersibility of the component active agent is critical to in vivo success. Thus, the ability to demonstrate redispersibility greatly aids in the solid dosage form design. That is the design of a solid dose form predictive of optimum in vivo performance characteristics.

Example 2

The purpose of this example was to evaluate the redispersibility properties of a solid dose nanoparticulate ketoprofen composition in an electrolyte solution. Ketoprofen, also known as m-benzoylhydratopic acid is a nonsteroidal anti-inflammatory analgesic. The drug is poorly water-soluble.

A ketoprofen nanoparticulate dispersion was prepared having 5% ketoprofen, 1% polyvinyl pyrrolidone (PVP) K29/32, and 0.2% dioctyl sodium sulfosuccinate (DOSS). The dispersion was prepared using a Dyno®-Mill (Type: KDL; Mfg.: Willy A Bachofen A G, Basel Switzerland) equipped with a 150 cc batch chamber using a 500 µm milling media of type Polymill500® for 2 hrs at 10° C.

The ketoprofen nanoparticulate dispersion (ketoprofen NCD) was then spray dried with mannitol, with a drug to mannitol ratio of 1:1 using a Büchi Mini Spray Dryer B-191 (Büchi, Switzerland). The redispersibility properties of the spray dried ketoprofen composition in water are shown below in Table 1.

TABLE 1

Redispersibility Properties of a Solid Dose Nanoparticulate Ketoprofen Composition in Water

| Time (days) | Mean (no sonication) | Mean (1 min. sonication) | $D_{50}$ (1 min. sonication) | $D_{50}$ (no sonication) | $D_{90}$ (1 min. sonication) | $D_{90}$ (no sonication) |
|---|---|---|---|---|---|---|
| 0 | 118 | 121 | 105 | 107 | 192 | 198 |
| 1 | 152 | 163 | 144 | 155 | 219 | 233 |

All measurements are in nanometers (nm).

The results of the redispersibility test show excellent redispersibility of the spray dried nanoparticulate composition.

The redispersibility properties of the same spray dried ketoprofen composition were then tested in electrolyte solutions, which mimic the conditions found in the human gastrointestinal tract. The results of these tests are shown in Table 2, below.

TABLE 2

Redispersibility Properties of a Solid Dose Nanoparticulate Ketoprofen Composition in Electrolyte Solutions

| Electrolyte Conc. (M) | Type | no sonic. Mean | No. sonic. Small % | No. sonic. Large % | 1 min. sonic. Mean | 1 min. sonic. Small % | No. sonic. Large % |
|---|---|---|---|---|---|---|---|
| 0 | — | 172 | 100 | 0 | 182 | 100 | 0 |
| 0.001 | HCl | 535 | 97 | 3 | 166 | 100 | 0 |
| 0.01 | HCl | 176 | 100 | 0 | 188 | 100 | 0 |
| 0.1 | HCl | 17756 | 2 | 98 | 5908 | 8 | 92 |
| 0.001 | NaCl | 178 | 100 | 0 | 191 | 100 | 0 |
| 0.01 | NaCl | 151 | 100 | 0 | 163 | 100 | 0 |
| 0.1 | NaCl | 186 | 100 | 0 | 204 | 100 | 0 |

All particle sizes are in nanometers (nm).

"Small" particles are defined as those below 1 micron (1000 nm) and "large" particles are those above 1 micron. Electrolyte concentrations of 0.001 M HCl, 0.01 M HCl, and 0.1 M HCl correspond to pH 3, pH 2, and pH 1, respectively. In the stomach, the pH ranges from slightly less than 2 (but typically greater than 1) up to 4 or 5. In the small intestine the pH can range from 4 to 6, and in the colon it can range from 6 to 8. Thus, a 0.01 M HCl concentration simulates typical acidic conditions found in the stomach. 0.1 M NaCl simulates the electrolyte concentration found throughout the body, including the intestine.

The results show that under acidic to neutral pH conditions, the nanoparticulate ketoprofen solid dose composition showed excellent redispersibility properties, with 100% of the nanoparticulate particles having a redispersed particle size of less than 1 micron. In addition, under all but the most acidic conditions of 0.1 M HCl (which are not typically representative of human gastric pH), the nanoparticulate ketoprofen solid dose composition showed excellent redispersibility properties, with almost 100% of the nanoparticulate particles having a redispersed particle size of less than 1 micron.

Example 3

The purpose of this example was to evaluate the redispersibility properties of a solid dose nanoparticulate MAP kinase inhibitor composition in electrolyte solutions.

5% (w/w) of Compound A, a poorly water-soluble MAP kinase inhibitor, 1% Plasdone® S630, and 0.2% DOSS were milled using a Dyno®-Mill (Type: KDL; Mfg.: Willy A Bachofen A G, Basel, Switzerland) equipped with a 150 cc batch chamber using a 500 µm milling media of type Polymill500® for 3 hrs at 10° C. Plasdone® S630 is a random copolymer of vinyl acetate and vinyl pyrrolidone.

The nanoparticulate MAP kinase inhibitor dispersion (NCD) was then spray dried at a drug to mannitol ratio of 1:1 using a Büchi Mini Spray Dryer B-191 (Büchi, Switzerland).

The redispersibility properties of the spray dried MAP kinase inhibitor in electrolyte solutions are shown below in Table 3 and in FIG. 2. A Horiba LA910 particle sizer was used to measure particle size. "Small" particles were defined as those below 1 micron and "large" particles were defined as those above 1 micron.

TABLE 3

Redispersibility Properties of a Solid Dose Nanoparticulate MAP
Kinase Inhibitor Composition in Electrolyte Solutions

| Electrolyte Conc. (M) | Type | no sonic. Mean | No. sonic. Small % | No. sonic. Large % | 1 min. sonic. Mean | 1 min. sonic. Small % | No. sonic. Large % |
|---|---|---|---|---|---|---|---|
| 0 | — | 99 | 100 | 0 | 99 | 100 | 0 |
| 0.001 | HCl | 100 | 100 | 0 | 100 | 100 | 0 |
| 0.01 | HCl | 105 | 100 | 0 | 106 | 100 | 0 |
| 0.1 | HCl | 4708 | 23 | 77 | 1901 | 52 | 48 |
| 0.001 | NaCl | 103 | 100 | 0 | 103 | 100 | 0 |
| 0.01 | NaCl | 101 | 100 | 0 | 101 | 100 | 0 |
| 0.1 | NaCl | 105 | 100 | 0 | 105 | 100 | 0 |

All particle sizes are in nanometers (nm).

The results show that the solid dose nanoparticulate MAP kinase inhibitor composition showed excellent redispersibility in all tested electrolyte media representative of in vivo conditions. Even at a higher acid concentration of 0.1 M HCl, the composition showed over 50% of the drug particles of the composition having a small particle size following 1 minute of sonication.

Example 4

The purpose of this example was to evaluate the redispersibility properties of a solid dose nanoparticulate angiogenesis inhibitor composition in water and in electrolyte solutions.

Nanocrystalline dispersions (NCD) of a poorly water-soluble angiogenesis inhibitor, Compound C, were made by milling the ingredients shown for each composition in Table 4. Samples A and B were milled on a Netzch Mill (Netzsch Inc., Exton, Pa.), having a LMZ 2L chamber, for 11 hrs. 500 micron PolyMill media was used. Processing temperatures ranged from 11.6° C. to 27.4° C. Samples C-E were milled on a Dyno® Mill, having a 150 cc chamber, at a temperature of 10° C. for 3 hours, also using 500 micron PolyMill media.

Following milling, the additives listed in Table 4 were added to the nanoparticulate dispersion until dissolved, followed by spraying of the dispersion over a fluidized mannitol excipient, also provided in Table 4, to form a solid dose composition. A Glatt GPCG-1 fluid bed processor (Glatt Air Technologies, Inc., Ramsey, N.J.) was used for this process.

TABLE 4

Spray Granulated Nanoparticulate Angiogenesis Inhibitor Compositions

| Sample | Formula | Particle Size of Nanocrystal Dispersion (nm) | Additives | Fluidized Mannitol |
|---|---|---|---|---|
| A | 15% Drug + 3.75% PVP K29/32 and 0.15% sodium lauryl sulfate (SLS) | mean 105 nm; $D_{90}$ of 167 nm | Drug: mannitol ratio of 1:0.75 | Pearlitol ® SD200 |
| B | 15% Drug + 3.75% PVP K29/32 and 0.15% SLS | mean 105 nm; $D_{90}$ of 167 nm | Drug: mannitol ratio of 1:0.75 | Pearlitol ® SD200 |
| C | 15% Drug + 3.75% PVP K29/32, 0.15% SLS, and 0.1% sodium ascorbate | mean of 101 nm; $D_{90}$ of 165 nm | Drug: mannitol ratio of 1:0.75 | Mannitol 35 |
| D | 15% Drug + 3.75% PVP K29/32, 0.15% SLS, and 0.1% sodium ascorbate | mean of 101 nm; 090 of 165 nm | Drug: mannitol ratio of 1:0.75 | Mannitol 35 |
| E | 15% Drug + 3.75% PVP K29/32, 0.15% SLS, and 0.1% sodium ascorbate | mean of 101 nm; $D_{90}$ of 165 nm | Drug: mannitol ratio of 1:0.75 and stabilizer DOSS ratio of 1:0.2 | Mannitol 35 |

Each composition A-E, comprising drug/excipient granules, was then milled to a uniform particle size in a Quadro Comill (Model 193; also called a cone mill, which comprises fixed stationary screens and a rotating impeller), to produce Compositions A2-E2. The milling process comprised passing the powder through the mill (one pass through, about 2-5 minutes).

The redispersibility, in water and various electrolyte solutions, was then measured for the solid dose nanoparticulate angiogenesis inhibitor compositions, both Compositions A-E (unmilled) and A2-E2 (milled), as shown in Table 5.

TABLE 5

Redispersibility of Solid Dose Nanoparticulate Angiogenesis Inhibitor Compositions
(Milled and Unmillled Granulate Compositions) in Water and Electrolyte Solutions

| Composition | Redisp. Media | No Sonication | | | 1 Min. Sonication | | |
|---|---|---|---|---|---|---|---|
| | | Mean (nm) | D90 (nm) | % Under 1000 nm | Mean (nm) | D90 (nm) | % Under 1000 nm |
| A (unmilled) | water | 5265 | 11776 | 26.2 | 1440 | 4717 | 70.8 |
| | 0.01 M HCl | 12160 | 27244 | 9.4 | 3034 | 6997 | 36.1 |
| | 0.01 M NaCl | 7487 | 15324 | 11.6 | 2274 | 6504 | 57.6 |
| A2 (milled) | Water | 5777 | 12463 | 23.0 | 2538 | 7547 | 62.9 |
| | 0.01 M HCl | 58519 | 236602 | 5.3 | 3573 | 7929 | 30 |
| | 0.01 M NaCl | 8341 | 17698 | 11 | 1975 | 5366 | 54.9 |
| B (unmilled) | Water | 8222 | 18365 | 18.5 | 4368 | 9033 | 51.5 |
| | 0.01 M HCl | 83643 | 264545 | 4.8 | 4238 | 9458 | 26.3 |
| | 0.01 M NaCl | 14863 | 33139 | 8 | 2579 | 6561 | 45.8 |
| B2 (milled) | Water | 18897 | 55523 | 14.2 | 2691 | 7294 | 50 |
| | 0.01 M HCl | 44037 | 103747 | 4.1 | 5161 | 11771 | 22.4 |
| | 0.01 M NaCl | 13514 | 29820 | 6.8 | 2547 | 6163 | 42.1 |
| C (unmilled) | Water | 3124 | 8088 | 46.9 | 422 | 645 | 93.4 |
| | 0.01 M HCl | 6713 | 14117 | 16.6 | 2471 | 6285 | 47 |
| | 0.01 M NaCl | 4103 | 9426 | 30.6 | 904 | 3006 | 80.4 |
| C2 (milled) | Water | 3150 | 8427 | 49 | 1071 | 3602 | 83.6 |
| | 0.01 M HCl | 8728 | 19180 | 17.1 | 3039 | 7626 | 43.3 |
| | 0.01 M NaCl | 4544 | 9896 | 25.5 | 1278 | 4345 | 75 |
| D (unmilled) | Water | 3094 | 7865 | 44.8 | 342 | 569 | 97.3 |
| | 0.01 M HCl | 9630 | 21697 | 14.8 | 2762 | 7043 | 45.3 |
| | 0.01 M NaCl | 4295 | 8561 | 20.6 | 1475 | 5034 | 73.6 |
| D2 (milled) | Water | 2162 | 5885 | 54.4 | 295 | 488 | 98.7 |
| | 0.01 M HCl | 8885 | 20181 | 16.9 | 1982 | 5087 | 51.7 |
| | 0.01 M NaCl | 4410 | 8710 | 19 | 1066 | 3420 | 75.9 |
| E (unmilled) | Water | 2186 | 7520 | 69.9 | 384 | 614 | 98.3 |
| | 0.01 M HCl | 2161 | 7812 | 73.4 | 297 | 492 | 99 |
| | 0.01 M NaCl | 2544 | 8755 | 68.1 | 357 | 588 | 98.5 |
| E (milled) | Water | 2711 | 9141 | 66.6 | 436 | 672 | 93.6 |
| | 0.01 M HCl | 2014 | 7608 | 75.9 | 291 | 483 | 99.1 |
| | 0.01 M NaCl | 2203 | 8075 | 74.1 | 292 | 484 | 99 |

The redispersibility results first show that redispersibility in water does not predict redispersibility in an electrolyte solution.

Second, the redispersibility results show only one sample, Sample E, showed good redispersibility in electrolyte media, with a redispersibility of 99.1% in 0.01 M HCl and 99% in 0.01 M NaCl. In contrast, Samples A-D showed redispersibility in 0.01 M HCl of from 22.4% (Sample B2) to 51.7% (Sample D2), and a redispersibility in 0.01 M HCl of from to 42.1% (Sample B2) to 80.4% (Sample C). The results are dramatic as the only difference between Sample E and Samples C and D was the presence (Sample E) or absence (Samples C and D) of DOSS.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. An in vitro method for evaluating a solid dosage form comprising:
    (a) dispersing a solid dosage form in a biorelevant medium, wherein the solid dosage form comprises at least one poorly water-soluble active agent, and wherein prior to incorporation into the solid dosage form, the active agent has an effective average particle size of greater than 2 microns;
    (b) measuring the particle size of the dispersed poorly water-soluble active agent; and
    (c) determining if the level of dispersibility is sufficient for in vivo effectiveness of the dosage form, wherein the level of dispersibility is sufficient for in vivo effectiveness of the dosage form if the dosage form disperses such that the particle size of the dispersed active agent particles is similar to the particle size of the active agent prior to incorporation into the solid dosage form,
    wherein the active agent is selected from the group consisting of an active agent for treating cystic-fibrosis, an active agent for treating asthma, an active agent for treating emphysema, an active agent for treating chronic bronchitis, an active agent for treating chronic obstructive pulmonary disease, and an active agent for treating tuberculosis.

2. The method of claim 1, wherein the dosage form is selected from the group consisting of dosage forms intended for oral, pulmonary, nasal, parenteral, rectal, local, and buccal delivery.

3. The method of claim 1, wherein prior to incorporation into the dosage form the active agent has an effective average particle size selected from the group consisting of greater than 5 microns, greater than 10 microns, greater than 15 microns, and greater than 20 microns.

4. The method of claim 1, wherein the biorelevant aqueous media is selected from the group consisting of electrolyte solutions of strong acids, salts of strong acids, strong bases, salts of strong bases, weak acids, salts of weak acids, weak bases, salts of weak bases, and mixtures thereof.

5. The method of claim 4, wherein the electrolyte solution is selected from the group consisting of an HCl solution having a concentration from about 0.001 to about 0.1 M, an NaCl solution having a concentration from about 0.001 to about 0.2 M, and mixtures thereof.

6. The method of claim 4, wherein the electrolyte solution is selected from the group consisting of about 0.1 M HCl or less, about 0.01 M HCl or less, about 0.001 M HCl or less, about 0.2 M NaCl or less, about 0.01 M NaCl or less, about 0.001 M NaCl or less, and mixtures thereof.

7. The method of claim 4, wherein the electrolyte solution is selected from the group consisting of 0.01 M HCl and 0.1 M NaCl.

8. The method of claim 1, wherein prior to incorporation into the dosage form the active agent has an effective average particle size selected from the group consisting of about 5 microns, about 10 microns, about 15 microns, and about 20 microns.

9. An in vitro method for evaluating a solid dosage form, comprising:
   (a) dispersing a solid dosage form in a biorelevant medium, wherein the solid dosage form comprises at least one poorly water-soluble active agent, and wherein prior to incorporation into the solid dosage form, the active agent has an effective average particle size of about 2 microns;
   (b) measuring the particle size of the dispersed poorly water-soluble active agent; and
   (c) determining if the level of dispersibility is sufficient for in vivo effectiveness of the dosage form, wherein the level of dispersibility is sufficient for in vivo effectiveness of the dosage form if the dosage form disperses such that the particle size of the dispersed active agent particles similar to the particle size of the active agent prior to incorporation into the solid dosage form,
   wherein the active agent is selected from the group consisting of an active agent for treating cystic-fibrosis, an active agent for treating asthma, an active agent for treating emphysema, an active agent for treating chronic bronchitis, an active agent for treating a chronic obstructive pulmonary disease and an active agent for treating tuberculosis.

10. The method of claim 9, wherein the dosage form is selected from the group consisting of dosage forms intended for oral, pulmonary, nasal, parenteral, rectal, local, and buccal delivery.

11. The method of claim 9, wherein the biorelevant aqueous media is selected from the group consisting of electrolyte solutions of strong acids, salts of strong acids, strong bases, salts of strong bases, weak acids, salts of weak acids, weak bases, salts of weak bases, and mixtures thereof.

12. The method of claim 11, wherein the electrolyte solution is selected from the group consisting of an HCl solution having a concentration from about 0.001 to about 0.1 M, an NaCl solution having a concentration from about 0.001 to about 0.2 M, and mixtures thereof.

13. The method of claim 11, wherein the electrolyte solution is selected from the group consisting of about 0.1 M HCl or less, about 0.01 M HCl or less, about 0.001 M HCl or less, about 0.2 M NaCl or less, about 0.01 M NaCl or less, about 0.001 M NaCl or less, and mixtures thereof.

14. The method of claim 11, wherein the electrolyte solution is selected from the group consisting of 0.01 M HCl and 0.1 M NaCl.

* * * * *

UNITED STATES PATENT AND TRADEMARK OFFICE
CERTIFICATE OF CORRECTION

PATENT NO. : 8,309,136 B2
APPLICATION NO. : 12/729018
DATED : November 13, 2012
INVENTOR(S) : Cooper et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 115 days.

Signed and Sealed this
Twenty-eighth Day of May, 2013

Teresa Stanek Rea
*Acting Director of the United States Patent and Trademark Office*